(12) United States Patent
Lisberg

(10) Patent No.: US 11,116,918 B2
(45) Date of Patent: Sep. 14, 2021

(54) DELIVERY SYSTEM FOR METERED DOSE INHALERS

(71) Applicant: Edward E. Lisberg, Chicago, IL (US)

(72) Inventor: Edward E. Lisberg, Chicago, IL (US)

(73) Assignee: ABITHAS, INC., Chicago, IL (US)

( * ) Notice: Subject to any disclaimer, the term of this patent is extended or adjusted under 35 U.S.C. 154(b) by 42 days.

(21) Appl. No.: 16/528,957

(22) Filed: Aug. 1, 2019

(65) Prior Publication Data

US 2019/0351159 A1     Nov. 21, 2019

Related U.S. Application Data

(63) Continuation-in-part of application No. 15/057,907, filed on Mar. 1, 2016, now abandoned.

(Continued)

(51) Int. Cl.
*A61M 15/00* (2006.01)
*A61M 11/00* (2006.01)

(52) U.S. Cl.
CPC ...... *A61M 15/0088* (2014.02); *A61M 11/003* (2014.02); *A61M 15/0025* (2014.02); *A61M 2205/121* (2013.01); *A61M 2205/44* (2013.01)

(58) Field of Classification Search
CPC .......... A61M 15/0088; A61M 15/0021; A61M 15/009; A61M 15/0086; A61M 2205/183;

(Continued)

(56) References Cited

U.S. PATENT DOCUMENTS 4,484,577 A    11/1984   Sackner et al.
4,790,305 A    12/1988   Zoltan et al.
(Continued)

FOREIGN PATENT DOCUMENTS

WO     WO-8303976 A1 * 11/1983 ........ A61M 15/0086

OTHER PUBLICATIONS

USPTO, Non-Final Office Action in U.S. Appl. No. 15/057,907, dated Nov. 27, 2018.
(Continued)

*Primary Examiner* — Jan Christopher L Merene
*Assistant Examiner* — Brian T Khong
(74) *Attorney, Agent, or Firm* — Siritzky Law, PLLC

(57) ABSTRACT

An accessory device for delivering medications from press and breath metered-dose inhalers (pMDIs), including those medications containing hydrofluoroalkane propellants. The device includes a collapsible flexible bag to which is attached a bidirectional mouthpiece and an adaptor that receives the press and breath MDI. The mouthpiece contains a reed that functions as an audible signal, and a screen to prevent inhalation of unwanted particles. The adaptor positions the press and breath MDI at an angle to direct the aerosol spray toward the center of the collapsible flexible bag. When the press and breath MDI is triggered, it discharges the aerosolized medication into the center of the collapsible flexible bag which is then inhaled by the user through the mouthpiece. This collapses the bag. The reed emits an audible sound if the user inhales above a predetermined flow rate to maximize medication delivery and ensure dose-to-dose consistency.

24 Claims, 10 Drawing Sheets

Related U.S. Application Data

(60) Provisional application No. 62/126,973, filed on Mar. 2, 2015.

(58) Field of Classification Search
CPC .......... A61M 2205/44; A61M 2205/75; A61M 11/06; A61M 16/0045; A61K 9/0073; A24F 1/30
See application file for complete search history.

(56) References Cited

U.S. PATENT DOCUMENTS

| | | | |
|---|---|---|---|
| 5,042,467 A | | 8/1991 | Foley |
| 5,318,016 A | * | 6/1994 | Mecikalski ....... A61M 15/0086 |
| | | | 128/200.14 |
| 5,842,467 A | * | 12/1998 | Greco ............... A61M 16/0078 |
| | | | 128/200.23 |
| 6,578,571 B1 | | 6/2003 | Watt |
| 6,595,206 B2 | | 7/2003 | Vito |
| 6,644,305 B2 | | 11/2003 | MacRae et al. |
| 6,655,380 B1 | | 12/2003 | Andersson et al. |
| 7,418,962 B1 | | 9/2008 | Rao |
| D717,424 S | | 11/2014 | Steelman et al. |
| 8,973,571 B1 | | 3/2015 | Gallem et al. |
| D835,260 S | | 12/2018 | Lisberg |
| 2002/0102033 A1 | * | 8/2002 | Antonacci ............. B65D 29/04 |
| | | | 383/117 |
| 2003/0010336 A1 | | 1/2003 | Vito |
| 2005/0005929 A1 | * | 1/2005 | Snyder .............. A61M 15/0086 |
| | | | 128/200.23 |
| 2006/0099149 A1 | | 5/2006 | Patel |
| 2006/0130839 A1 | | 6/2006 | Bassovitch |
| 2006/0260606 A1 | * | 11/2006 | Coifman ............. A61M 15/009 |
| | | | 128/200.14 |
| 2008/0141437 A1 | * | 6/2008 | Braunecker ............. A61F 7/032 |
| | | | 2/206 |
| 2008/0308102 A1 | * | 12/2008 | Davies .............. A61M 15/0003 |
| | | | 128/203.15 |
| 2010/0224185 A1 | | 9/2010 | Anderson et al. |
| 2011/0232636 A1 | | 9/2011 | Von Hallen et al. |
| 2013/0195384 A1 | * | 8/2013 | Dais .................... B65D 33/255 |
| | | | 383/63 |
| 2013/0276781 A1 | | 10/2013 | Steelman et al. |
| 2013/0291862 A1 | * | 11/2013 | Eagle ................ A61M 15/0065 |
| | | | 128/203.12 |
| 2014/0093192 A1 | * | 4/2014 | Dais ....................... B65D 33/28 |
| | | | 383/65 |
| 2014/0338662 A1 | * | 11/2014 | Vecellio-None ........................... |
| | | | A61M 16/0816 |
| | | | 128/200.23 |
| 2015/0266622 A1 | * | 9/2015 | Tseng .................... B65D 33/18 |
| | | | 383/37 |
| 2015/0360824 A1 | * | 12/2015 | Porchia ................ B65D 33/007 |
| | | | 383/42 |

OTHER PUBLICATIONS

USPTO, Final Office Action in U.S. Appl. No. 15/057,907, dated May 10, 2019.

* cited by examiner

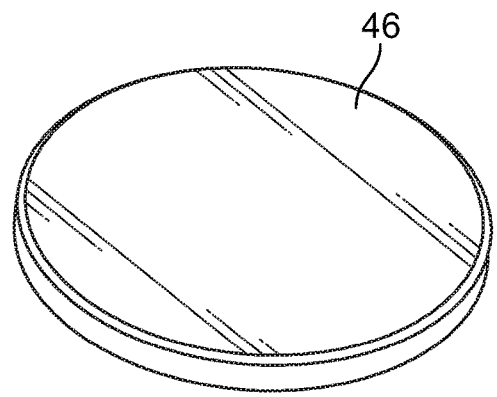 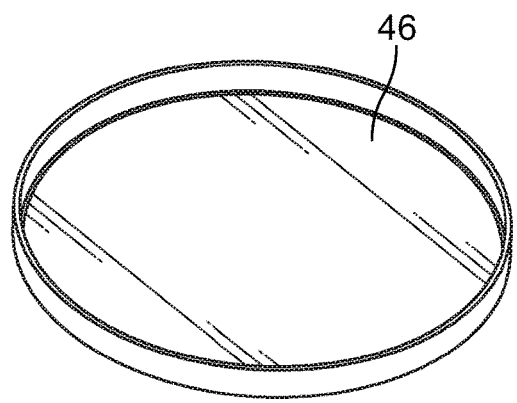
FIG. 14　　　　　　　　　FIG. 15
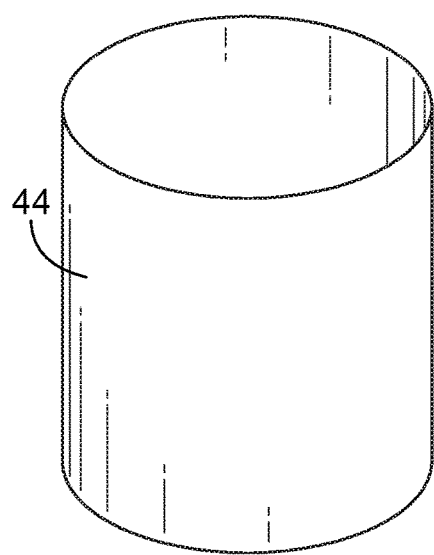 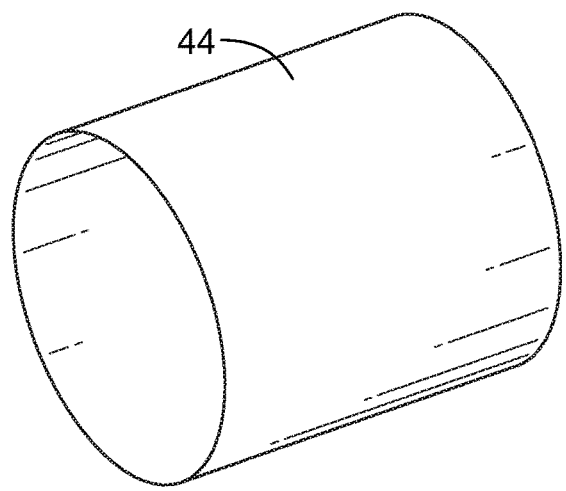
FIG. 16　　　　　　　　　FIG. 17

DELIVERY SYSTEM FOR METERED DOSE INHALERS

CROSS REFERENCE TO RELATED APPLICATION

This application is a continuation in part of U.S. application Ser. No. 15/057,907 filed Mar. 1, 2016, currently pending, which is based on and claims the priority of U.S. provisional patent application Ser. No. 62/126,973 filed Mar. 2, 2015.

FIELD OF THE INVENTION

The present invention relates to inhalations systems for delivering a dose of aerosolized medication from metered-dose inhaler devices, for inhalation by a patient.

BACKGROUND AND SUMMARY OF THE INVENTION

Delivery of pharmaceuticals via inhalation has long been considered the standard of care for the treatment patients with acute and chronic respiratory diseases such as asthma and chronic obstructive pulmonary disease ("COPD"). Over the past 50 years, press and breath metered-dose inhalers ("pMDIs") have become the mainstay of inhaled treatment for such patients and are widely known and used by the medical profession. Experience clearly shows that while widely prescribed, many patients cannot or will not use pMDIs as intended.

As illustrated in FIG. 1, a pMDI 10 comprises an original manufacture assembled pressurized canister 11 containing a drug/propellant and possibly excipients mixture 12. The canister 11 is mounted in an actuator 13. A metering valve stem 14 extends out from the canister 11 and is received in an actuator seat 15. The metering valve dispenses the drug substance/propellant 12 contained within the canister 11, through an actuator nozzle 16, generating a mist or plume 17 which exits through the actuator exit tube 18.

Suboptimal pMDI inhalation technique contributes to poor lung deposition of medication, poor disease control, adverse asthma and COPD outcomes, and increased medical costs. Studies demonstrate the inability of both patients and healthcare providers to properly use pMDIs. Due to the inability of patients to properly use pMDIs, a number of devices ("Spacers") have been proposed to assist in pMDI use. In laboratory test conditions, many Spacers have appeared to improve pMDI aerosol delivery to the lower airways; however, outside of the laboratory, experience demonstrates that many patients cannot consistently use these Spacers as intended. A major factor contributing to the lack of pMDI Spacer user consistency is that device users cannot determine if they consistently both (1.) have fully inhaled the complete dose following pMDI actuation, and (2.) have inhaled at a low inspiratory flow rate necessary for effective delivery of aerosolized medication from pMDIs.

Once a pMDI canister is triggered, the most important patient centered factors that relate to optimal lung delivery of medication are: (1) initiation of inhalation prior to 80% of total lung capacity (within approximately the first 1-2 seconds after medication is aerosolized), and (2) that the user generates a sufficiently low inspiratory flow rate to effectively deliver proper sized optimal aerosol particles into the lung alveoli. The subjective terms "long" or "slowly" are common instructions by manufacturers on pMDI medication inserts, but these terms have been of little value in ensuring proper patient inhalation technique. Spacer and pMDI devices which lack an effective inspiratory flow signal or fail to provide effective visual and auditory feedback regarding complete dose inhalation may result in medication dosing that is not constant dose-to-dose or patient-to-patient.

Prior art devices were designed for use with the previous generation of chlorofluorocarbons ("CFC") propellant containing pMDI medications. CFC propellants have been completely banned by international protocol for use, and all current pMDI use hydrofluoroalkane ("HFA") propellants. With change in propellants, this required design of new pMDI medication canisters, metering valve stems, and actuators. Some of these prior art devices have built in a single "one size fits all" actuator seat. No single size actuator seat can properly fit nor properly function with the different pMDI metering valve stems with current hydrofluoroalkane ("HFA") propellant containing pMDIs. Canister stem-actuator mismatch leads to improper and suboptimal pMDI particle size generation, essentially making the device/canister poorly or non-functional, and thus a less efficient device compared to the instant inventive device. Under 21 CFR part 3, the Food and Drug Administration (FDA) considers each pMDI drug canister and actuator device as unique "combination products", each such product is subject to individual approval and regulation. These prior art devices which require users to remove drug canisters from their original actuators completely fail to adequately address these elements and do not match optimal characteristics of the inventive device.

For example, U.S. Pat. No. 4,484,577 issued to Sackner et al. and entitled "Drug Delivery Method and Inhalation Device Therefor" describes an inhalation device in which the inhaler actuator/canister assembly 21 is disassembled and the canister is inserted into a universal, single actuator located within the device mouthpiece. The canister is mounted at 90° to the mouthpiece and airbag. The medication is directed from the mouthpiece end, away from the user, into the airbag. This device does not provide a device for use with the original manufacturer canister/actuator combination press and breath MDI but rather is limited to the insertion of the canister into the Sackner device actuator in the mouthpiece.

Similarly, U.S. Pat. No. 5,318,016 issued to Mecikalski entitled "Inhalation Device" describes a device similar to U.S. Pat. No. 4,484,577 in which the original manufacturer pMDI actuator/canister is disassembled and the canister is inserted into the Mecikalski device universal single sized actuator. The device cannot be used with any intact, original manufacturer pMDI. The device requires users remove canisters from the pMDI and insert the canisters into a vertically oriented device actuator. The actuator/canister cannot function unless in the fully vertical 90° position relative to the cap 10. The guide 18 is rotated to a vertical position providing finger grips 32 for the user to grasp and more easily push down and trigger the canister in the device actuator.

Other devices illustrate dispersing the drug from pMDIs toward the user's mouthpiece in a "direct flow" rather than in a direction away from the mouthpiece, a "reverse flow". The direct flow of the medication is not as effective as dispersing the drug away from the mouthpiece in a reverse flow. Examples of such prior devices are U.S. Patent Application Publication Number 2013/0291862 to Eagle entitled "Spacer and Components Therefore" and U.S. Patent Application Publication Number 2013/0276781 to Steelman et al. entitled "Inhalation Devices and Systems and Methods Including the Same." Both of these devices illustrate dispersing the medication in a direct flow from the end of the device opposite the user's mouthpiece toward the mouthpiece.

Several of the prior art devices such as Mecikalski, Eagle and Steelman et al. cited above also lack an inspiratory flow reed and fail to provide any type of signal regarding the user's inspiratory flow rate. The inspiratory flow rate is the most critical technique factor which determines the effectiveness of lower airway delivery of inhaled medication delivery from a pMDI canister after the pMDI is triggered. A properly designed inspiratory flow rate signal, which functions outside the laboratory as intended for patient use, is critical to ensure effective medication delivery from pMDIs.

The shortcomings of the prior art devices are that they lack proper actuator seat sizing for the different pMDI metering valve stems, an inspiratory flow signal (i.e., not capable of ensuring puff-puff dose equivalency), an easy means for determining if medication is fully inhaled, or have a simple mechanism for patients to easily operate.

Applicant's device is not a pMDI, but rather a device to be used with intact, originally manufactured press and breath MDI combination products to assist in the proper delivery of aerosolized medication from pMDIs. Applicant's invention addresses the shortcomings of the prior art by providing a simple, efficient, easy to use device for patients to consistently deliver containing medications from pMDIs. Applicant's device ensures consistent puff-to-puff delivery of inhaled medications via an adaptor optimized for pMDI medications, and an effective inspiratory flow reed signal. The device includes a collapsible flexible bag to which is attached a bidirectional mouthpiece and an adaptor that receives the pMDI medication. The mouthpiece contains a reed that functions as an audible signal and a screen to prevent inhalation of unwanted particles. When the pMDI is triggered, it discharges the medication into the collapsible flexible bag. The adaptor is placed at an angle with respect to the center axis of the bag so that the medication delivery is optimized towards the center of the bag instead of along the walls of the bag. This minimizes the amount of medication essentially wasted and not available for inhalation. The medication is inhaled from the collapsible flexible bag, through the mouthpiece, directly into the respiratory tract, collapsing the bag. The reed emits an audible sound if the user inhales above a predetermined rate to maximize medication delivery and ensure dose-to-dose consistency. The user has instant feedback regarding correct inhalation from pMDI medication regarding: (1) whether or not each dose of medication is completely inhaled (the bag fully collapses upon complete inhalation), and (2) whether or not each dose is inhaled at a rate to achieve efficient lower airway aerosol medication delivery (a whistle sounds if the user breathes in too fast).

DESCRIPTION OF THE DRAWINGS

FIG. 14 is a bottom view of the bottom end cap.

FIG. 15 is a top view of the bottom end cap.

FIG. 16 is a front perspective view of the collapsible flexible bag.

FIG. 17 is a front perspective view of the collapsible flexible bag when in a horizontal position.

DESCRIPTION OF THE PREFERRED EMBODIMENT

Figure 1:
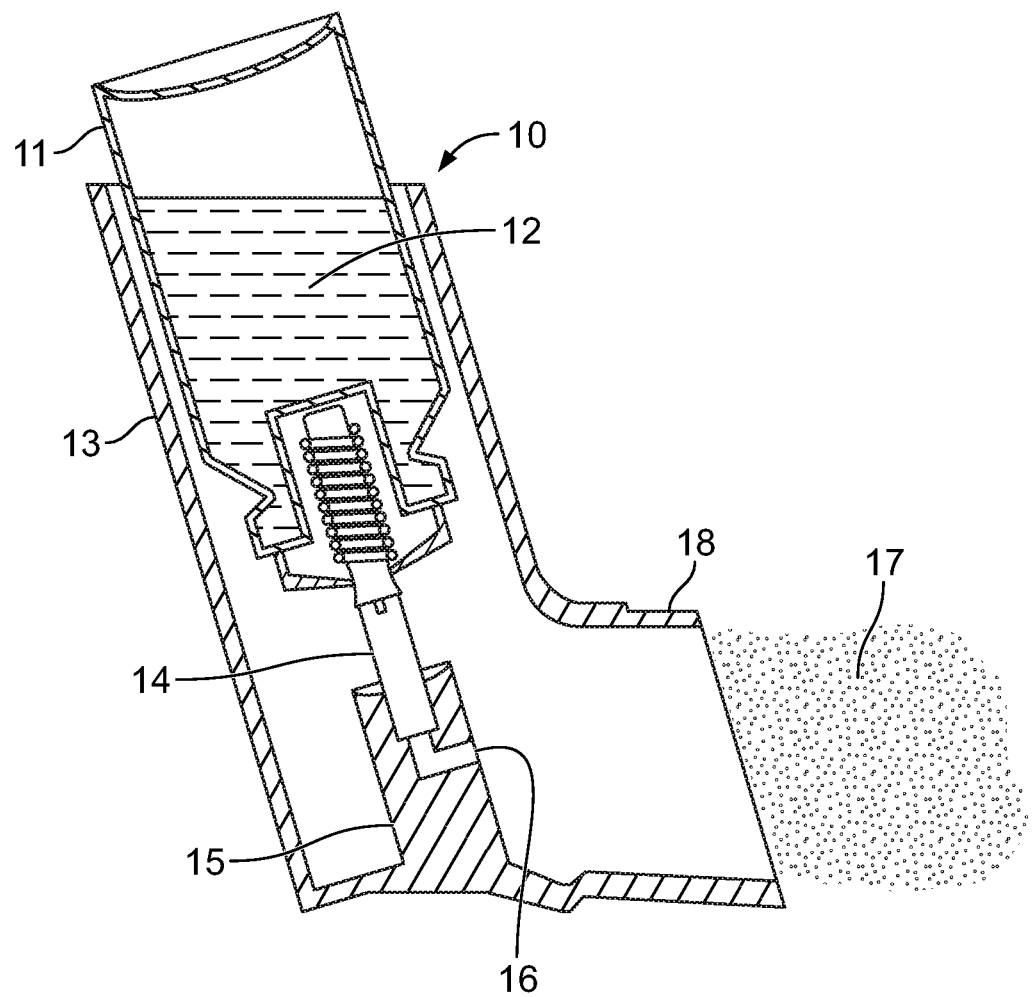
FIG. 1 illustrates the prior art of a press and breath MDI showing the drug/propellant containing canister seated in an actuator.
Figure 2:
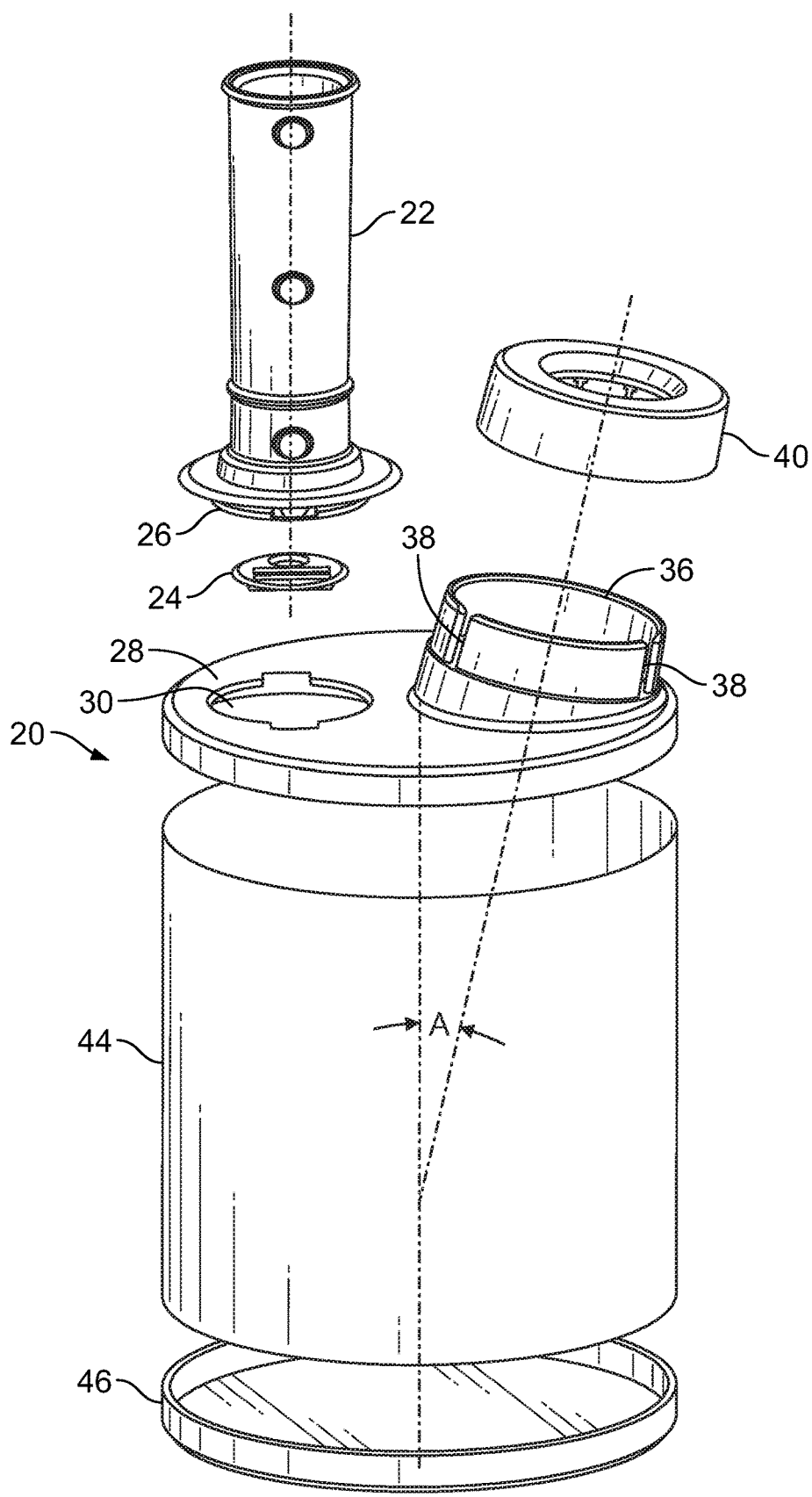
FIG. 2 is an exploded view of the inventive delivery device for press and breath metered dose inhalers.

As described above, FIG. 1 illustrates the components of the intact press and breath MDI (pMDI) 10. Turning to FIG. 2, there is illustrated an exploded view of a delivery device 20 for press and breath metered dose inhalers 10. There is a mouthpiece 22, containing a screen 48, that has a reed 24 inserted into a lower end 26 of the mouthpiece 22. The mouthpiece 22 is inserted into a top end cap 28 through opening 30. The opening 30 has two opposite rectangular slots 32 which receive locking tabs 34 at the lower end 26 of the mouthpiece 22 (seen in FIG. 6).

The top end cap 28 also has an upstanding collar 36 angularly disposed with respect to the top planar surface of the top end cap 28. The top end cap 28 is made from high density polyethylene (HDPE) and is substantially flat except for the perimeter that may have an upstanding or tapered edge or other surface imperfections due to the plastic molding process. There are a pair of vertically disposed keyways 38 cut into the wall of the upstanding collar 36. A pMDI adaptor 40 is mounted on the collar 36. There are keys 42 (FIG. 10) that are received in the keyways 38 to properly align the pMDI adaptor 40 with the collar 36 so that the pMDI actuator 13 is properly positioned for use in the pMDI adaptor 40. There is a channel 41 in the pMDI adaptor that receives the collar 36 in tight engagement to firmly, but releasably retain the pMDI adaptor 40 on the collar 36. A collapsible flexible bag 44 is located below the top end cap 28. The collapsible flexible bag 44 is preferably made from a low density metallocene polyethylene ("LDPE") However other similar materials exhibiting the same characteristics may also be available. At the bottom of the metallocene LDPE bag 44 is a bottom end cap 46. The top end cap 28 has a circumferential collar that closely receives the top of the metallocene LDPE bag 44. The bottom end cap 46 has a similar circumferential collar that receives the bottom of the metallocene LDPE bag 44. The low density metallocene polyethylene exhibits at least two important characteristics. First it allows the collapsible flexible bag 44 to attach to the top end cap 28 and bottom end cap 46 which are made from high density polyethylene (HDPE). This creates an airtight seal between the top and bottom end caps 28 and 46 and the collapsible flexible bag 44. Second the metallocene LDPE exhibits antibacterial properties. The volume of the collapsible flexible bag 44 when in the expanded position should preferably be between 42.11-42.72 cubic inches (approximately 690-700 cubic cm).

Figure 3:
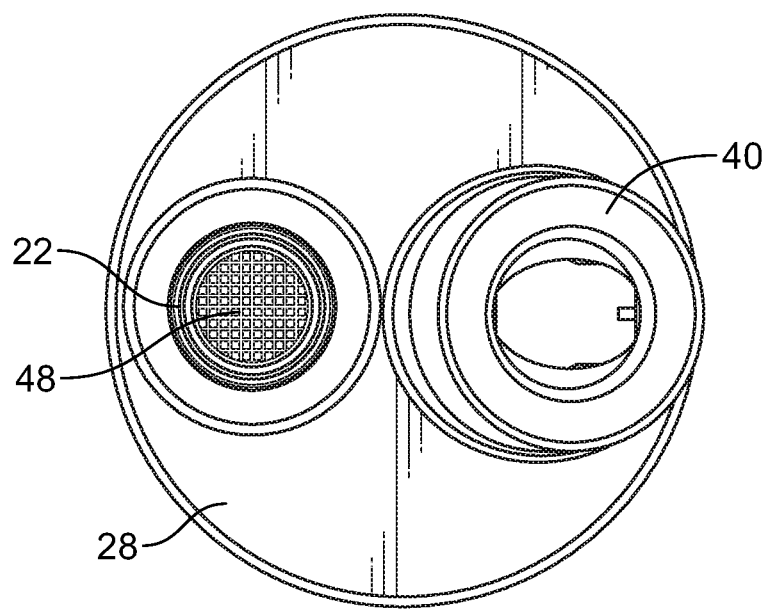
FIG. 3 is a top view of the top end cap of the device with the mouthpiece and adaptor attached.
Figure 4:
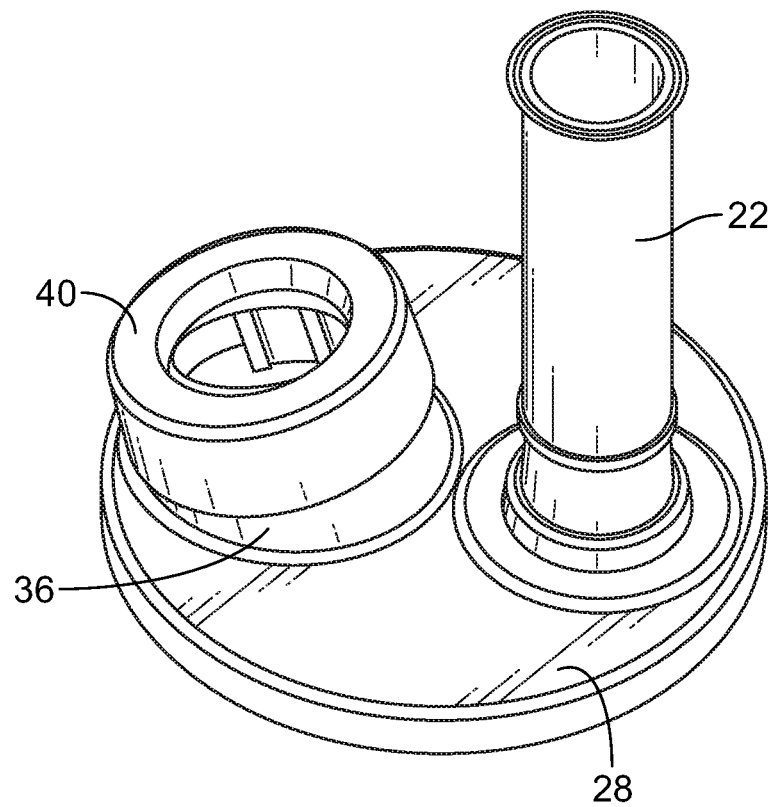
FIG. 4 is a top perspective of the top end cap with the adaptor and mouthpiece attached.

As seen in FIG. 3, the mouthpiece 22 contains the screen 48 in its central channel. FIGS. 3 and 4 illustrate the mouthpiece 22 and pMDI adaptor 40 mounted on the top end cap. An airtight seal is provided between the mouthpiece 22 and the top end cap 28 and the pMDI adaptor 40 and the upstanding collar 36.

Figure 5:
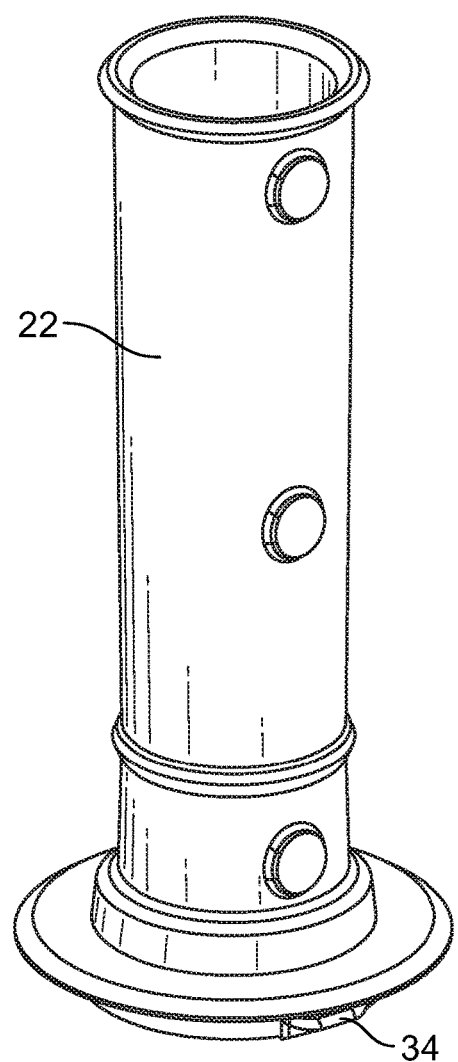
FIG. 5 is a side view of the mouthpiece.
Figure 6:
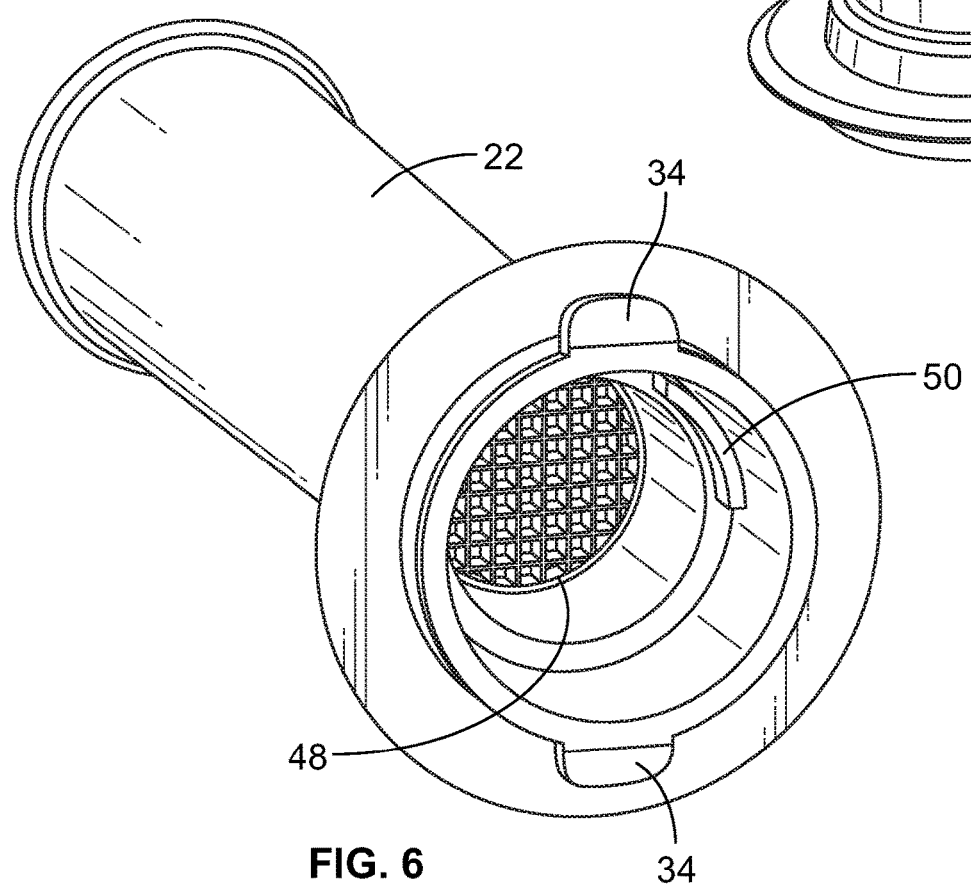
FIG. 6 is a rear perspective view of the mouthpiece showing the screen component of the mouthpiece.
Figure 7:
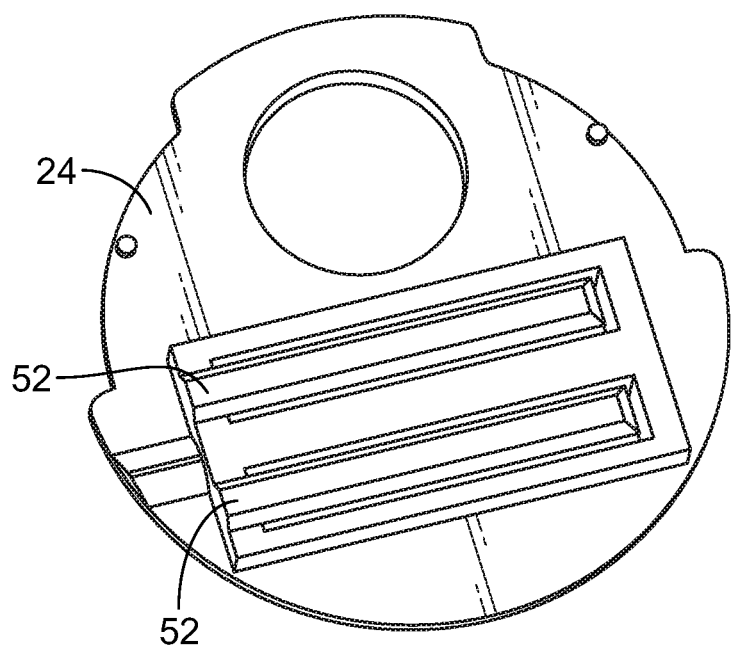
FIG. 7 is top view of the reed.
Figure 8:
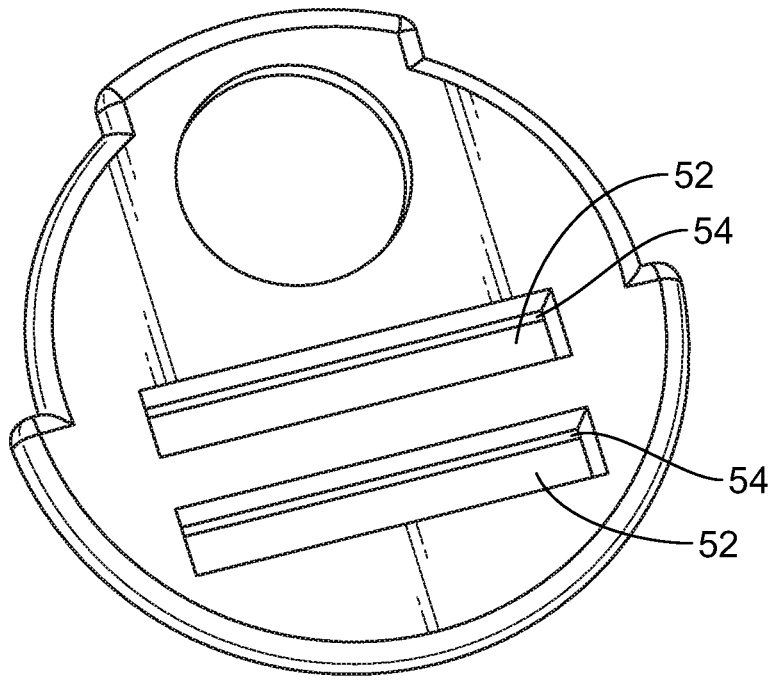
FIG. 8 is a bottom view of the reed.

FIGS. 5 and 6 more clearly illustrate the mouthpiece 22. The locking tabs 34 are clearly illustrated at opposite sides of the bottom of the mouthpiece 22. As seen in FIG. 6, there is an internal collar 50 for the reed attachment that receives and correctly positions the reed 24 within the bottom of the mouthpiece 22. FIGS. 7 and 8 illustrate the reed 24. There are a pair of vibrating members 52 mounted in slots 54. One end of the each of the vibrating members 52 is fixed to the reed body while the opposite end is free to vibrate. Other types of reed designs can be used as is commonly known in the art. The purpose of the reed is to vibrate and produce an audible sound if the air flow past the reed exceeds a preset level.

Figure 9:
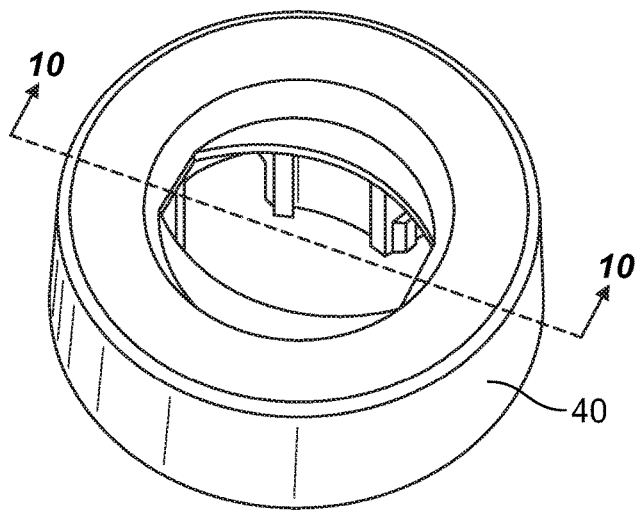
FIG. 9 is a top perspective view of the pMDI adaptor.
Figure 10:
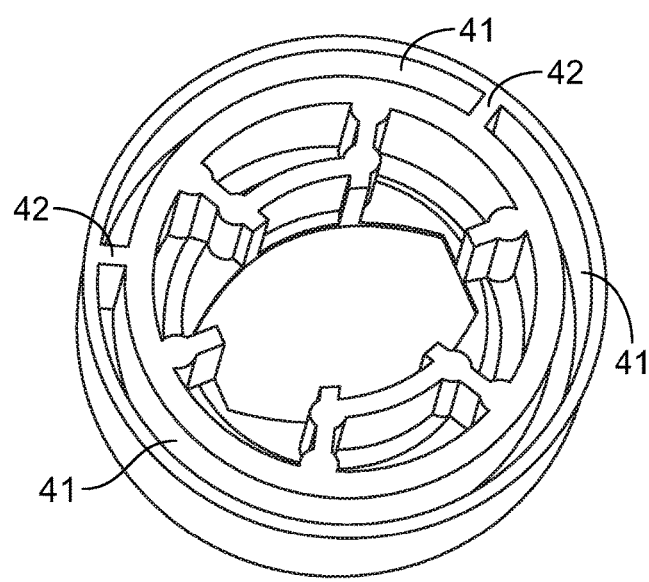
FIG. 10 is a bottom perspective view of the pMDI adaptor.
Figure 11:
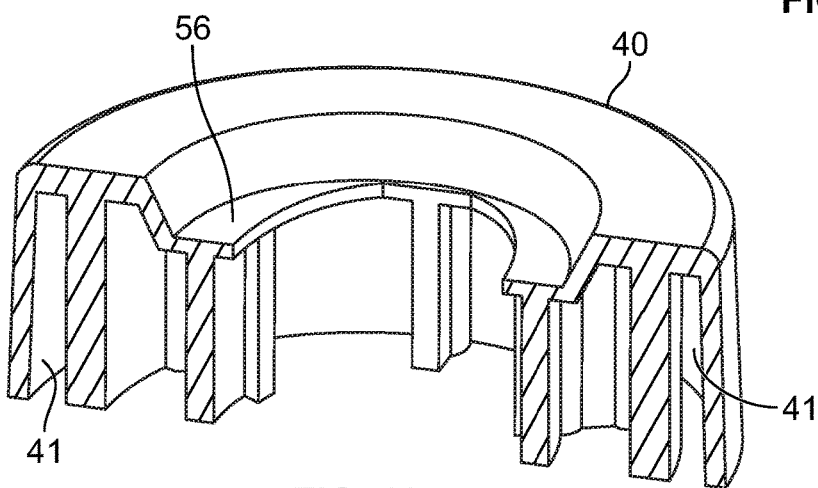
FIG. 11 is a cross sectional view of the adaptor taken along lines 11-11 of FIG. 9.

FIGS. 9-11 illustrate the pMDI adaptor. The adaptor 40 is preferably made from a flexible material that is sufficiently rigid to retain its shape when inserted onto the collar 36 but has an innermost ring 56 with a centrally disposed slot that is flexible enough to receive various size pMDI actuator exit tubes 18. The pMDI actuator is snugly received in the slot in the innermost ring 56 so that there are no gaps between the innermost ring and the pMDI actuator thus forming a substantially airtight seal between the innermost ring 56 and the pMDI adaptor 40.

Figure 12:
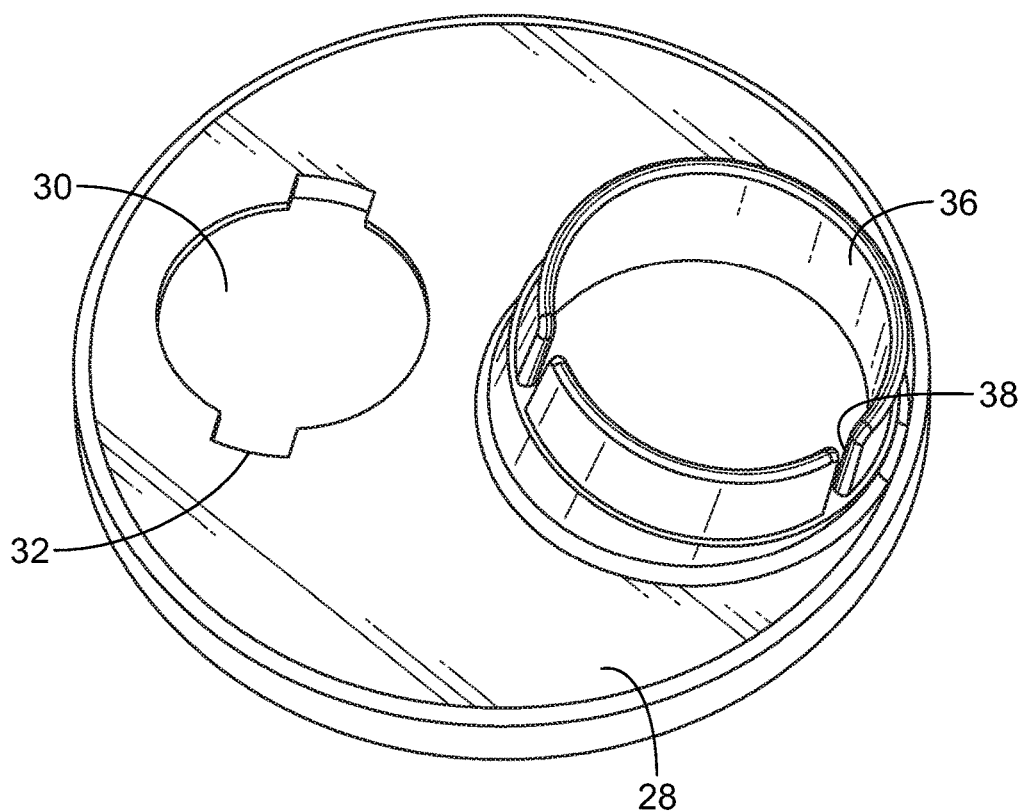
FIG. 12 is a top perspective view of the top end cap.

FIG. 12 clearly illustrates the opening 30 with the slots 32 cut in the top end cap 28. These receive the locking tabs 34 in the bottom of the mouthpiece 22. Once the locking tabs 34 are inserted, the mouthpiece is rotated so that the locking tabs 34 firmly lock the mouthpiece to the top end cap 28. The collar 36 is also shown with the keyways 38. These receive the keys 42 in the underside of the pMDI adaptor 40.

Figure 13:
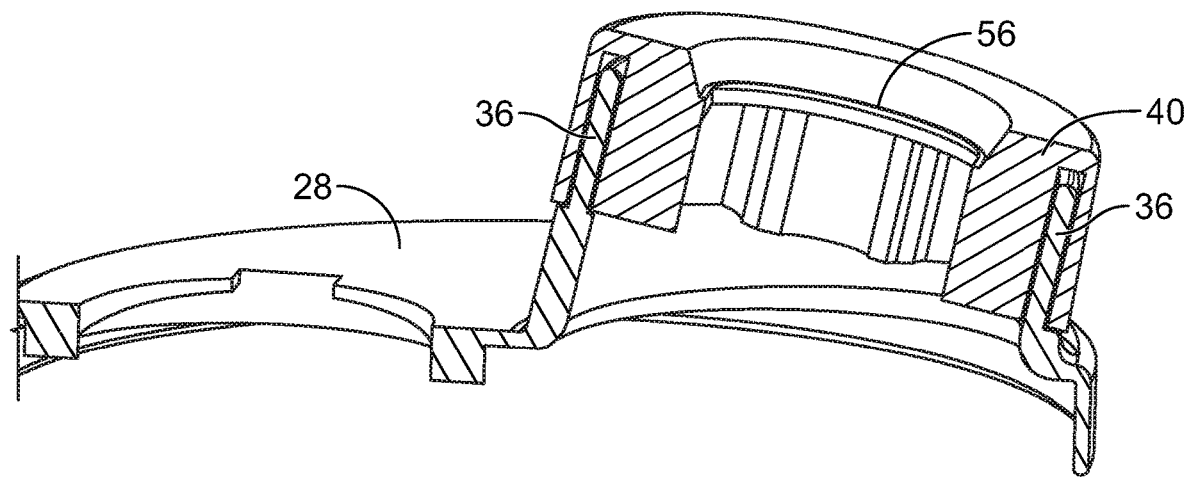
FIG. 13 is cross sectional view taken along line 13-13 of FIG. 12.

FIG. 13 is a cross sectional view of a portion of the pMDI adaptor 40 mounted to the collar 36 which in turn is mounted to or integrally formed with the top end cap 28. FIGS. 14 and 15 illustrate bottom end cap 14. As seen in FIG. 15 there is an upstanding collar or rim that closely receives in an airtight fitting the bottom of the flexible bag 44.

Figure 18:
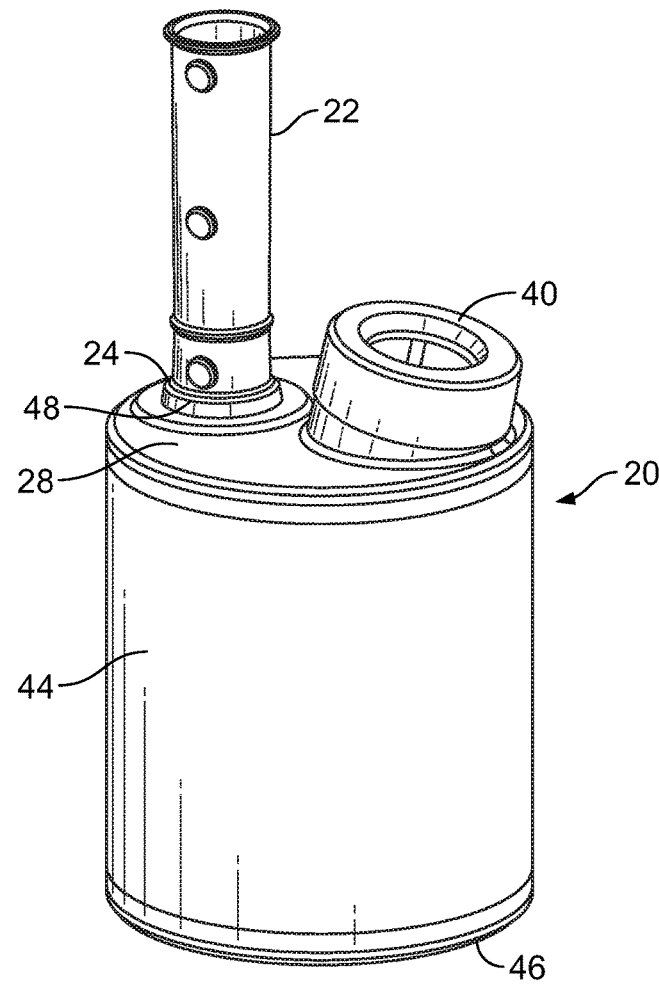
FIG. 18 is a front perspective view of the assembled device in the vertical position.

FIGS. 16 and 17 illustrate the cylindrical shape of the metallocene LDPE flexible bag 44. FIG. 18 illustrates the assembled delivery device for pMDIs 20. The mouthpiece 22 and pMDI adaptor 40 are fitted onto the top end cap 28. Inside of the mouthpiece 22 are the reed 24 and screen 48. The metallocene LDPE flexible bag 44 is securely fitted to the top end cap 28 and bottom end cap 46.

Figure 19:
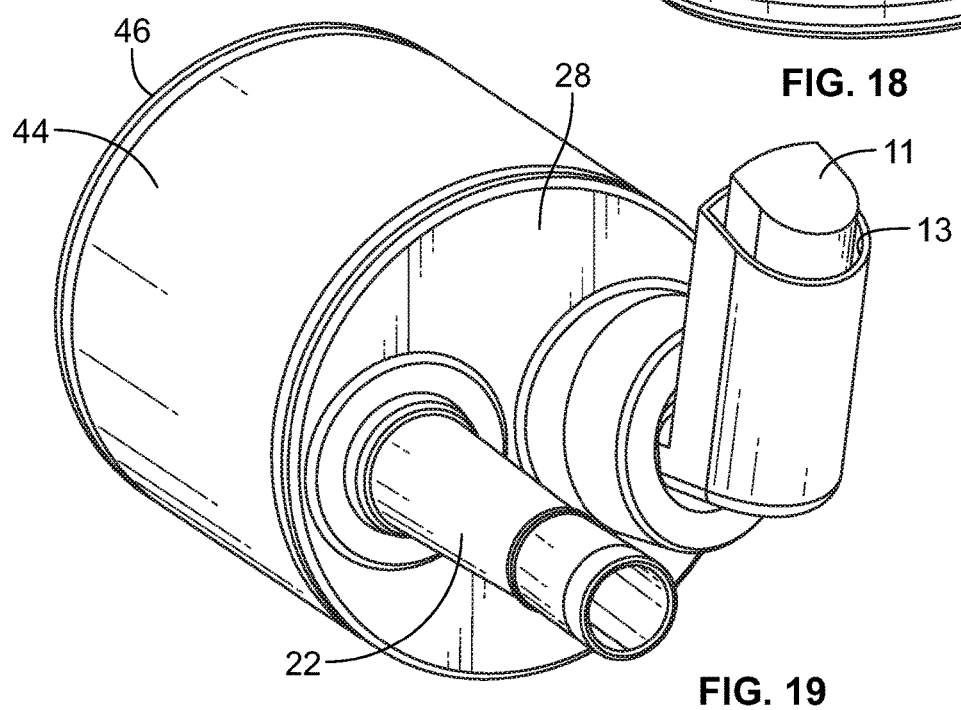
FIG. 19 is a perspective view of the inventive device in the horizontal position with the press and breath MDI actuator inserted into the adaptor.
Figure 20:
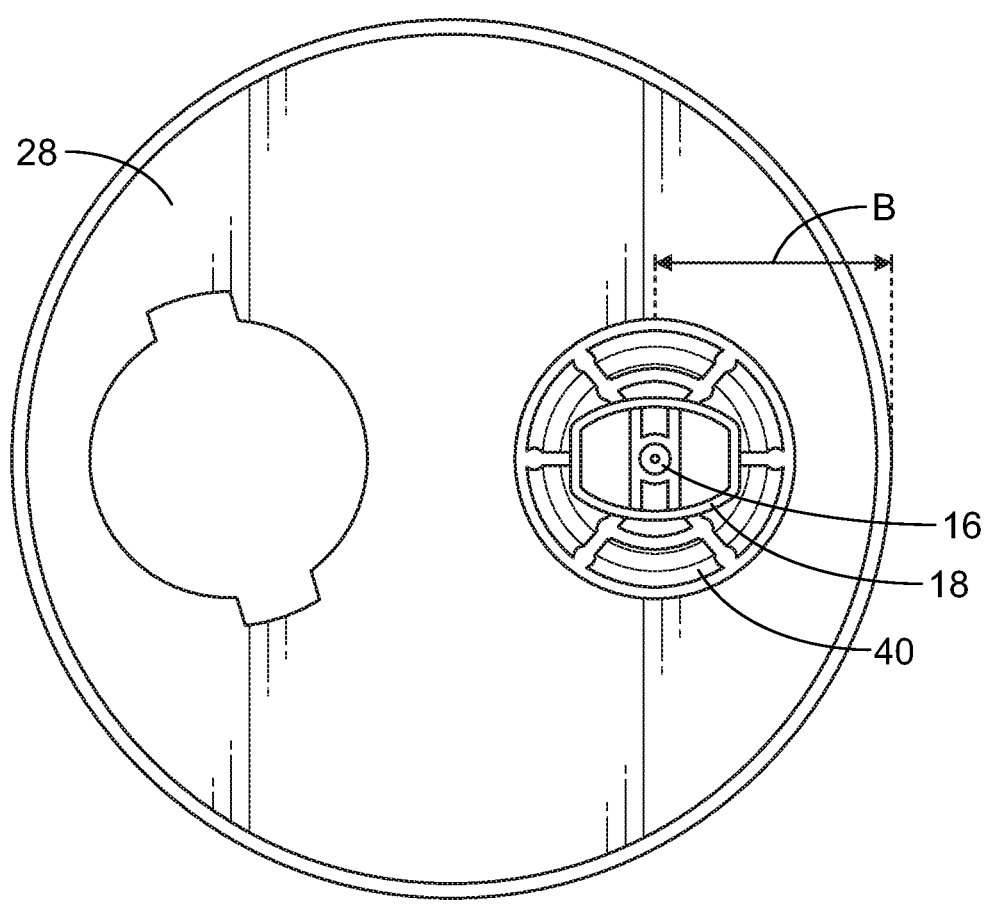
FIG. 20 is a bottom view of the top end cap with the pMDI actuator inserted.

FIG. 19 is similar to FIG. 18 except that a pMDI 10 is inserted into the pMDI adaptor 40. As see in FIG. 2, the upstanding collar 36 is angularly disposed at an angle "A" of between 8° to 18° and preferably 13° with respect to the center line along the axis of the flexible bag 44. The angle is determined by the location of the collar 36 from the perimeter of the end cap 28 so that the spray or plume of medication from the canister is disbursed into the center of the flexible bag 44 when the flexible bag 44 is in the expanded position in a direction toward the center of the bottom end cap 46. This optimizes spray plume distribution within the flexible bag 44 and minimizes the spray hitting the side walls of the flexible bag 44. For example, when the device 20 is held horizontally, and with a diameter of the end cap being 3.085 inches, the distance from the circumference of the end cap 28 to a line extending horizontally from the center of actuator nozzle 16 is between 0.984 inches to 1.22 inches as illustrated in FIG. 20 by the letter "B".

To use the device 20, the mouthpiece 22 is inserted via the locking tabs 34 into slots 32 and rotated to lock the mouthpiece to the top end cap 28. The user inserts the pMDI actuator 13 into the innermost ring 56 so that it is properly aligned with the opening in the innermost ring 56 and the collar 36. The user opens the bag 44 fully. The user then depresses the pMDI canister 11, which then generates an aerosolized plume of medication into the metallocene LDPE bag 44. As the actuator exit tube 18 is properly aligned in the collar 36, it results in the plume 17 being directed toward the center of the metallocene flexible bag 44. The user inhales through mouthpiece 22, generating negative pressure in bag 44 and causing aerosolized medication to flow into the user's respiratory tract, thereby collapsing the metallocene flexible bag 44. The inspiratory flow reed 24 signals if the user inhales above the predetermined flow rate, above 1.0 liter/sec. After inhalation and 10 second breathhold, the user manually opens and expands the bag 44 to allow for a subsequent pMDI actuation cycle. The device 20 provides two indicators if the device is used properly. The first signal is a visual signal that indicates whether the user has fully inhaled the medication. This is indicated by the user seeing that the bag is fully collapsed. The second indicator is an audio signal indicating if the user incorrectly inhaled the medication. This is indicated by the reed in the device emitting a whistling or other audible sound if user inhales too fast for proper medication delivery to the lungs.

Thus, there has been provided a delivery assist device for press and breath metered dose inhalers for providing aerosolized drug to a user through inhalation that provides for the receipt of various sized original manufactured, pre-assembled pMDIs. It also provides two indicators for the user to make sure that the full dose of medication is inhaled and that the rate of inhalation is not at a flow rate that exceeds recommended flow rates. While the invention has been described in conjunction with a specific embodiment, it is evident that many alternatives, modifications and variations will be apparent to those skilled in the art in light of the foregoing description. Accordingly, it in intended to embrace all such alternatives, modifications and variations as fall within the spirit and scope of the claims.

What is claimed is:

1. An accessory delivery device for press-and-breathe metered dose inhalers, wherein a press-and-breathe metered dose inhaler comprises an actuator and a canister distinct from the actuator, the canister containing at least a drug, the device comprising:

a flexible collapsible airbag having an open top end and a closed bottom end;

a top end cap having a top surface, with a first opening and a second opening in the top surface, the top end cap being connected to the open top end of the flexible collapsible airbag;

a tubular mouthpiece having a proximal end suitable to place in a user's mouth, and a distal end mounted in the first opening of said top surface, the tubular mouthpiece in fluid communication with the flexible collapsible airbag;

a warning indicator, wherein said warning indicator provides a signal based on exceeding a predetermined inhalation flow rate through the tubular mouthpiece;

an upstanding collar in the second opening in the top end cap, the upstanding collar being disposed at a fixed angle offset from perpendicular to the top surface of the top end cap; and an adaptor mounted on the upstanding collar, the adaptor having a centrally disposed flexible member, an opening in the centrally disposed flexible member adapted to receive a portion of the actuator of the press-and-breathe metered dose inhaler, wherein, when activated, the press-and-breathe metered dose inhaler dispenses an aerosol spray containing a drug via an actuator exit tube of the actuator through the adaptor in a direction away from the top end cap and into the flexible collapsible airbag, wherein the adaptor positions the actuator exit tube at the fixed angle offset from perpendicular to the top surface of the top end cap.

2. The device of claim 1, wherein the fixed angle of the collar to the top surface of the top end cap is between 8 degrees and 18 degrees.

3. The device of claim 1, wherein the tubular mouthpiece protrudes vertically from the top surface of the top end cap.

4. The accessory delivery device of claim 1, and further comprising a flexible sealing member mounted in the centrally disposed flexible member having a slot constructed and adapted to receive the actuator of the press-and-breathe metered dose inhaler in fluid tight engagement.

5. The accessory delivery device of claim 1, and further comprising a bottom end cap constructed and adapted to seal the bottom end of the flexible collapsible airbag.

6. The accessory delivery device of claim 5, wherein the top end cap and the bottom end cap comprise high density polyethylene.

7. The accessory delivery device of claim 6, wherein the flexible collapsible airbag comprises low density polyethylene.

8. The accessory delivery device of claim 7, wherein the flexible collapsible airbag comprises metallocene low density polyethylene.

9. The accessory delivery device of claim 1, wherein said warning indicator produces an audible sound when a flow rate of air passing through the tubular mouthpiece exceeds the predetermined inhalation flow rate.

10. The accessory delivery device of claim 9, wherein said warning indicator produces a whistling sound when the flow rate of air passing through the tubular mouthpiece from the flexible collapsible airbag exceeds the predetermined inhalation flow rate.

11. The device of claim 9, wherein the warning indicator comprises a reed that vibrates to produce said audible sound when the flow rate of air passing through the tubular mouthpiece exceeds the predetermined inhalation flow rate.

12. The accessory delivery device of claim 1, wherein the mouthpiece comprises locking tabs in the distal end and the first opening comprises slots to receive the locking tabs whereby the mouthpiece is removably attached to the first opening.

13. The accessory delivery device of claim 1, wherein the collar comprises keyways and the adaptor comprises internal keys that are received in the keyways to align the adaptor with the top end cap to align the opening in the centrally disposed flexible member to receive the actuator of the press-and-breathe metered dose inhaler.

14. The accessory delivery device of claim 1, wherein the flexible collapsible airbag gives a visual indication that the aerosol spray containing the drug has been inhaled when the airbag is collapsed.

15. The accessory delivery device of claim 1, and further comprising a channel in the press-and-breathe metered dose inhaler adaptor to receive the collar to securely attach the press-and-breathe metered dose inhaler adaptor to the collar.

16. The device of claim 1, wherein the portion of the actuator comprises an actuator exit tube of the actuator.

17. The device of claim 1, wherein an airtight seal is provided between the top end cap and the open top end of the flexible collapsible airbag.

18. The device of claim 17, wherein the airtight seal is provided by a seal surrounding the top end cap.

19. The device of claim 1, wherein the bottom end of the flexible collapsible airbag is sealed to prevent passage of air into and out from the flexible collapsible airbag from the bottom end.

20. The device of claim 1, wherein the warning indicator is mounted in the tubular mouthpiece.

21. The device of claim 1, further comprising:
a filter within the tubular mouthpiece.

22. The device of claim 1, wherein the adaptor is constructed and adapted to fit multiple different sized inhaler actuators.

23. The device of claim 1, wherein the upstanding collar is disposed at the fixed angle offset from perpendicular to the top surface of the top end cap when the inhaler is activated.

24. An accessory delivery device for a press-and-breathe metered dose inhaler, wherein the press-and-breathe metered dose inhaler comprises an actuator and a canister distinct from the actuator, the canister containing at least a drug, the device comprising:

a flexible collapsible airbag having an open top end and a closed bottom end;

a top end cap having a top surface, with a first opening and a second opening in the top surface, the top end cap being connected to the open top end of the flexible collapsible airbag;

a tubular mouthpiece having a proximal end suitable to place in a user's mouth, and a distal end mounted in the first opening of said top surface, the tubular mouthpiece in fluid communication with the flexible collapsible airbag;

an upstanding collar in the second opening in the top end cap, the upstanding collar being disposed at a fixed angle offset from perpendicular to the top surface of the top end cap, wherein the fixed angle is between 8 degrees and 18 degrees;

an adaptor mounted at the fixed angle on the upstanding collar, the adaptor having a centrally disposed flexible member, an opening in the centrally disposed flexible member adapted to receive a portion of the actuator of the press-and-breathe metered dose inhaler, wherein, when activated, the press-and-breathe metered dose inhaler dispenses an aerosol spray containing the drug via an actuator exit tube of the actuator, through the adaptor in a direction away from the top end cap and into the flexible collapsible airbag, wherein the adaptor is constructed and adapted to fit multiple different sized inhaler actuators; and a flexible sealing member mounted in the centrally disposed flexible member having a slot constructed and adapted to receive the actuator of the press-and-breathe metered dose inhaler in fluid tight engagement, wherein the adaptor positions the actuator exit tube at the fixed angle offset from perpendicular to the top surface of the top end cap.

* * * * *